(12) United States Patent
Wasowski

(10) Patent No.: US 8,273,114 B2
(45) Date of Patent: Sep. 25, 2012

(54) GROUNDED PRESSURE COOLING

(75) Inventor: Peter Z. Wasowski, Kamuela, HI (US)

(73) Assignee: Vasper Systems LLC, Kamuela, HI (US)

( * ) Notice: Subject to any disclaimer, the term of this patent is extended or adjusted under 35 U.S.C. 154(b) by 1009 days.

(21) Appl. No.: 12/091,939

(22) PCT Filed: Nov. 3, 2006

(86) PCT No.: PCT/US2006/042939
§ 371 (c)(1),
(2), (4) Date: Apr. 29, 2008

(87) PCT Pub. No.: WO2007/056130
PCT Pub. Date: May 18, 2007

(65) Prior Publication Data
US 2008/0234788 A1   Sep. 25, 2008

Related U.S. Application Data

(60) Provisional application No. 60/734,605, filed on Nov. 7, 2005.

(51) Int. Cl.
*A61F 7/00* (2006.01)
(52) U.S. Cl. .................................... 607/104; 606/201
(58) Field of Classification Search .......... 606/201; 428/78; 601/151, 152; 607/96, 104
See application file for complete search history.

(56) References Cited

U.S. PATENT DOCUMENTS

| | | |
|---|---|---|
| 620,679 A | 3/1899 | Shryock |
| 2,495,316 A | 9/1950 | Clark et al. |
| 3,211,153 A | 11/1961 | Gambetti |
| 3,317,650 A | 5/1967 | Padellford |
| 3,596,134 A | 7/1971 | Burke |
| 3,744,555 A | 7/1973 | Fletcher et al. |
| 3,995,621 A | 12/1976 | Fletcher et al. |
| 4,138,743 A | 2/1979 | Elkins et al. |
| 4,149,529 A | 4/1979 | Copeland et al. |
| 4,691,762 A | 9/1987 | Elkins et al. |
| 4,884,304 A | 12/1989 | Elkins |
| 5,033,136 A | 7/1991 | Elkins |
| 5,092,317 A | 3/1992 | Zelikovski |
| 5,571,075 A | 11/1996 | Bullard |
| 6,109,338 A | 8/2000 | Butzer |
| 6,149,618 A | 11/2000 | Sato |
| 6,178,562 B1 | 1/2001 | Elkins |
| 6,209,144 B1 | 4/2001 | Carter |
| 6,230,501 B1 | 5/2001 | Bailey et al. |

(Continued)

FOREIGN PATENT DOCUMENTS
WO   PCT/US96/20639 A1   10/1997

*Primary Examiner* — Laura Bouchelle
(74) *Attorney, Agent, or Firm* — File-EE-Patents.com; Jay A. Chesavage

(57) ABSTRACT

A chiller is coupled to a plurality of cuffs suitable for application to extremities of a human subject, each cuff having an outer support belt with an adjustable diameter and an inner bladder having an inlet port and an outlet port. The bladder has one surface constrained by the support belt and an opposite surface for application of pressure and cooling to an enclosed human extremity. The plurality of cuffs are connected to the cooler with a series of outlet ports and inlet ports such that the chiller causes the cuffs to be pressurized with a coolant which provides vascular restriction and cooling to increase the formation of human growth hormone.

23 Claims, 13 Drawing Sheets

U.S. PATENT DOCUMENTS

| | | |
|---|---|---|
| 6,551,347 B1 | 4/2003 | Elkins |
| 6,589,194 B1 | 7/2003 | Calderon et al. |
| 6,683,779 B2 | 1/2004 | Ober |
| 6,695,762 B1 * | 2/2004 | Mah et al. ................. 600/20 |
| 6,695,872 B2 | 2/2004 | Elkins |
| 6,757,916 B2 | 7/2004 | Mah et al. |
| 6,871,878 B2 | 3/2005 | Miros |
| 7,001,417 B2 | 2/2006 | Elkins |
| 7,089,995 B2 | 8/2006 | Koscheyev et al. |
| 7,107,629 B2 | 9/2006 | Miros et al. |
| 7,135,007 B2 | 11/2006 | Scott et al. |
| 7,198,093 B1 | 4/2007 | Elkins |
| 7,509,692 B2 | 3/2009 | Elkins |
| 7,565,705 B2 | 7/2009 | Elkins et al. |
| 7,641,623 B2 | 1/2010 | Biondo et al. |
| 7,896,910 B2 | 3/2011 | Schirrmacher et al. |
| 2001/0018604 A1 | 8/2001 | Elkins |
| 2001/0034545 A1 | 10/2001 | Elkins |
| 2001/0034546 A1 | 10/2001 | Elkins |
| 2001/0039439 A1 | 11/2001 | Elkins et al. |
| 2002/0019657 A1 | 2/2002 | Elkins |
| 2002/0138033 A1 | 9/2002 | Elkins |
| 2003/0229385 A1 | 12/2003 | Elkins |
| 2004/0167594 A1 | 8/2004 | Elkins |
| 2004/0267168 A1 | 12/2004 | Feng |
| 2005/0070405 A1 * | 3/2005 | Egger ..................... 482/78 |
| 2005/0094348 A1 | 5/2005 | Hattori |
| 2005/0126578 A1 | 6/2005 | Garrison et al. |
| 2005/0143797 A1 | 6/2005 | Parish et al. |
| 2006/0122544 A1 | 6/2006 | Ciluffo |
| 2006/0128538 A1 | 6/2006 | Sato et al. |
| 2006/0142128 A1 | 6/2006 | Sato |
| 2006/0191049 A1 | 8/2006 | Elkins et al. |
| 2006/0191063 A1 | 8/2006 | Elkins et al. |
| 2006/0201522 A1 | 9/2006 | Sato |
| 2006/0229661 A1 | 10/2006 | Sato |
| 2006/0270530 A1 | 11/2006 | Sato |
| 2006/0281611 A1 | 12/2006 | Sato |
| 2009/0221406 A1 | 9/2009 | Sato |

* cited by examiner

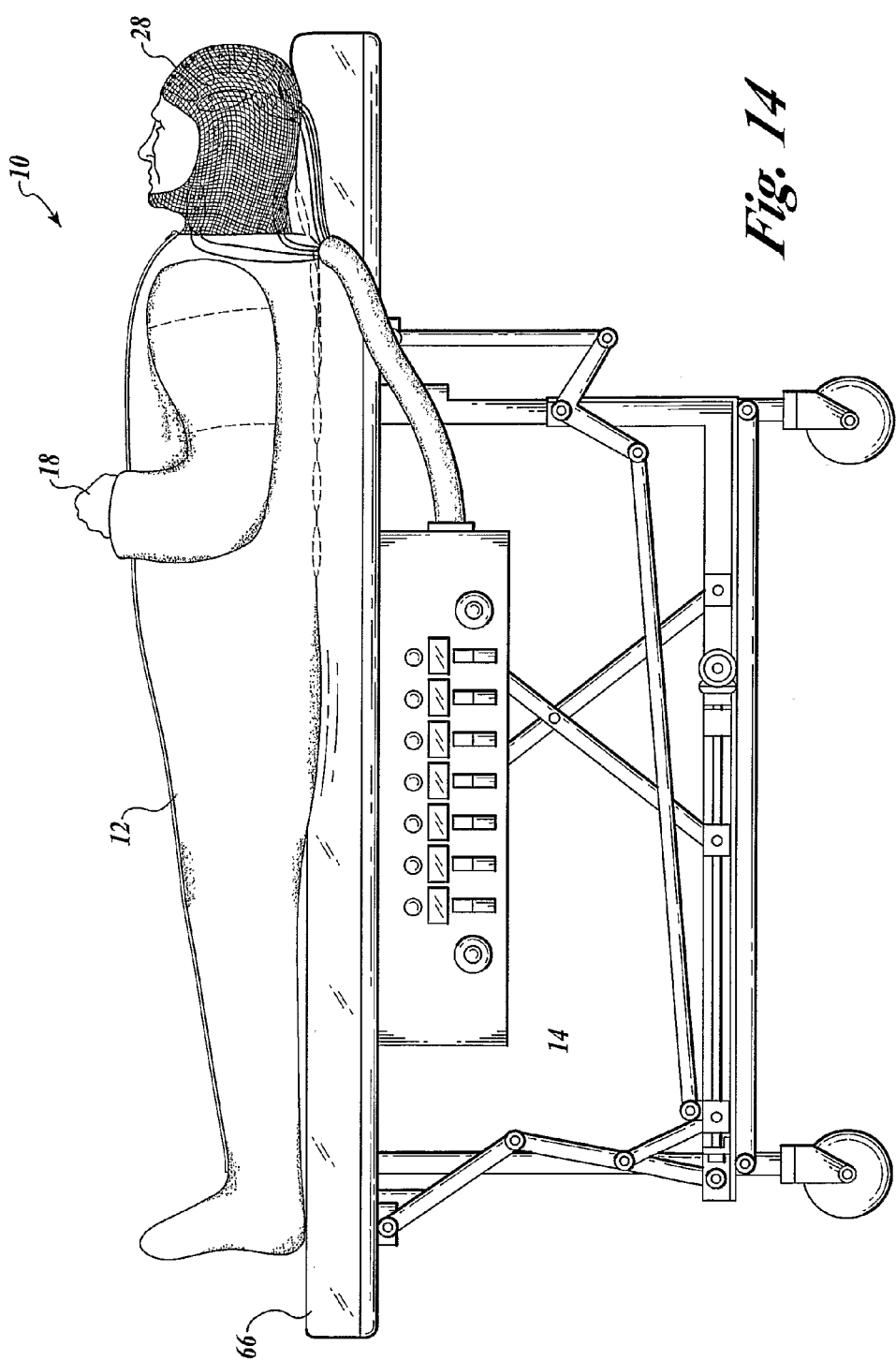

GROUNDED PRESSURE COOLING

PRIORITY DATA

The present application claims priority of International Patent Application Serial No. PCT/US2006/042939 filed on Nov. 3, 2006, which claims priority of U.S. Provisional patent application No. 60/734,605 filed Nov. 7, 2005, the contents of which are incorporated in their entirety.

BACKGROUND OF THE INVENTION

This invention relates to personal cooling, compression and grounding. In particular, the invention relates to increasing vascular performance of humans by lowering the core body temperature, compression of the blood vessels, and grounding of the body.

The background art is characterized by U.S. Pat. Nos. 620,679; 3,211,153; 3,317,650; 3,596,134; 3,596,134; 3,744,555; 4,149,529; 5,092,317; 5,571,075; 6,109,338; 6,149,618; 6,683,779; 6,757,916; and 7,089,995 and U.S. Patent Application Nos. 2004/0167594; 2004/0267168; 2005/0094348; and 2006/0122544; the disclosures of which patents and patent applications are incorporated by reference as if fully set forth herein.

Restriction of blood flow by applying compression has been shown to speed up muscle growth and muscle strength. The invention of U.S. Pat. No. 6,149,618 is limited, however, in that applying too much compression to the circumference of an extremity of a human body can be dangerous, because an embolism can result. Under these conditions, a blood clot can form, break off and become lodged in the brain or heart. Moreover, in the absence of precisely controlled core body cooling, reducing the rate at which blood circulates in an extremity can produce an unbearable amount of pain for most people.

The background art is also characterized by the products of Life Enhancement Technologies, Inc. (LET). (LET) has developed and patented a line of personal cooling products for medical, military, industrial and consumer applications. One of these products is Flexitherm™, a proprietary liquid heat transfer system made of a thin, flexible, conductive material, which transports fluid to provide direct conductive cooling. LET products embody technologies disclosed in U.S. Pat. Nos. 4,138,743; 4,691,762; 4,884,304; 5,033,136 and 6,551,347; the disclosures of which patents are incorporated by reference as if fully set forth herein.

The background art is also characterized by published articles. Relevant articles include Ober, C., *Grounding the Human Body to Neutralize Bioelectrical Stress from Static Electricity and EMF's*, EDS Journal; Becker, R. O, *The Body Electric*; Becker, R. O., *Cross Currents* and Metz, C. et al., Moderate hypothermia in patients with severe head injury: cerebral and extracerebral effects, Comment in J. Neurosurg. 1997, May, 85(5):911-914.

What is needed is an apparatus and method for increasing vascular performance of humans by simultaneously lowering core body temperature, compression of blood vessels, and grounding of the body in a controlled way.

BRIEF SUMMARY OF THE INVENTION

One purpose of the invention is to prevent heat stress and perspiration during exercise. Another purpose of the invention is to increase human growth hormone release. Yet another purpose of the invention is to allow the body to maintain its natural bio/electric flow. Yet another purpose of the invention is use in emergency medical (ambulance) applications for treatment of spine and head injuries.

Electrical grounding of the human body results in significant benefits in restoring the bio/electrical levels to their natural state. One purpose of the invention is to facilitate electrical grounding of the human body with smart spheres, which in a preferred embodiment are multi-functional, thin, compliant metallic devices which also channel a coolant liquid and measure pulse and body temperature.

Another purpose of the invention is to precisely control the pressure applied to the blood vessels of the extremities, thus safely restricting the blood flow which will result in higher amounts of growth hormone being released into the body. Growth hormone release has many restorative properties, such as balancing the body's hormonal function, burning excess fat and optimizing the metabolic rate. High levels of growth hormone also contribute to the formation of additional collateral circulation, thus vascular performance is significantly increased. In a preferred embodiment of the invention, the pressure that is applied to the body is in the range 178 milimeters mercury (mm Hg) to 238 mm Hg and is applied at relatively short intervals. Preferably, pressure settings are controlled by automatic fluidic valves with a manual override to ensure that a safe and correct pressure is applied to the human body.

Another purpose of the invention is to precisely control the applied pressure in order to prevent tissue damage. In a preferred embodiment, the apparatus measures the blood pressure prior to each use of the apparatus and ensures that the maximum pressure does not exceed 122 percent of the systolic blood pressure. Preferably, smart spheres placed on the distal extremities of the body of the user measures the distal extremity pulse every about 33 seconds during a use protocol and reports the pulse values to a control unit. If the pulse becomes too weak, the control unit reduces the amount of pressure applied to the user's body. Another purpose of the invention is to facilitate treatment of geriatric and pediatric patients using an apparatus that comprises smart spheres to ensure comfortable and multifunctional control.

One advantage of preferred embodiments of the invention is that core cooling during exercise prevents heat stress and perspiration. Evaporation of perspiration is the only natural way the body can lower its core temperature through the skin. In order to achieve perspiration, as much as forty percent of the blood flow is shunted from the muscle tissue to the skin surface which results in much lower blood flow in the muscles. This causes decreased elimination of lactic acid from the muscles and decreased delivery of oxygenated blood to the muscles, resulting in increased pain and discomfort associated with rigorous exercise. With preferred embodiments of the invention, there is no need for the body to sweat during exercise, thus the active muscles maintain full blood flow levels, lactic acid is removed at much more rapid pace, the delivery of oxygenated blood to the muscles is maintained at optimum levels, resulting in the exercise experience being free of discomfort and pain, with immediate post exercise recovery.

Another advantage of preferred embodiments of the invention is to increase blood density through the application of specific core body cooling gradients. Thus, the amount of pressure to the blood vessels during exercise can be reduced when compared to background art methods, to facilitate a desired growth hormone release. With preferred embodiments of the invention, the amount of pressure applied to the blood vessels is controlled in order to avoid complete occlusion of the vessels. Core body cooling, preferably utilizing the precisely applied and temperature regulated spheres, results in increased density of the blood, thus the amount of pressure applied to the blood vessels is decreased, avoiding the dangers associated with complete occlusion of the blood vessels.

Yet another advantage of preferred embodiments of the invention is that applying pressure to the blood vessels during exercise, along with cooling and grounding, significantly lowers or eliminates the risks. Core body cooling and grounding with vascular pressure during exercise maintains the normal body bio/electric flow patterns, by preventing perspiration and by releasing the static electrical charge to the ground. The subject performing the exercise protocol is therefore clear headed and not in a stress situation.

Another advantage of preferred embodiments of the invention is that electrical grounding during exercise, along with core body cooling and applied vascular pressure provides the electrical channel for the release of static electrical charge from the body, as well as delivery to the body of the Earth's neutral electrons. The human body was designed to be in direct contact with the ground. Electrical grounding allows the body to maintain its natural bio/electric flow and thus its physiologic functions are maintained at the optimal levels.

In a preferred embodiment, the invention is an apparatus and method for increasing vascular performance of humans by lowering core body temperature, compression of blood vessels, and grounding of the body. Preferably, the invention comprises grounded pressure cooling of a portion or all of the human body. In another preferred embodiment, the invention is an apparatus for treating an exercising human body, said apparatus comprising means for lowering the core body temperature, means for compressing the body's blood vessels, and means for grounding the body. In a preferred embodiment, the invention is a method for treating an exercising human body, said method comprising lowering the core body temperature, compressing the body's blood vessels, and grounding the body.

In use, the invention is operated by applying means for absorbing heat and exerting controlled pressure to the limbs of a human subject; electrically connecting the human subject to the ground; and causing the human subject to exercise.

In a preferred embodiment, the invention is an apparatus that comprises: a compression/cooling garment for installation on a human body, and a core body cooling and grounding unit, said core body cooling and grounding unit comprising a display having a user interface and a processor that is operated in accordance with a software program. Preferably, said compression garment comprises cooling spheres. Preferably, said cooling and grounding unit comprises a compressor and a condenser and an umbilical cord that connects said compression garment to said compressor and said condenser.

In a preferred embodiment, the invention is a method for increasing vascular performance of a human body by lowering core body temperature, compression of blood vessels, and grounding of the body. Preferably, the method comprises using a coolant that is in a temperature range from about 44 degrees F. to about 56 degrees F. (measured as it is leaving the chiller within core body cooling and grounding unit 14) to lower the core body temperature is lowered by about 2 or 3 degrees F. to about 96 F as stated below. In a preferred embodiment, the method also comprises compressing the blood vessels of the body's upper arms and legs by applying a pressure in the range from about 178 mm Hg to about 238 mm Hg to the exterior of the upper arms and legs, and by grounding the body to the earth. Preferably, a core body temperature of about 96 degrees F. is achieved. Preferably, a pressure of about 238 mm Hg pressure (maximum) is applied for up to about six minutes, but the applied pressure may vary with the initial measured systolic blood pressure of the user.

In a preferred embodiment, the invention is an apparatus that comprises: a compression/cooling garment for installation on a human body, said compression/cooling garment comprising the following components: two upper arm fluidic cuff and belt assemblies, each upper arm fluidic cuff and belt assembly comprising an upper arm blood pressure cuff and an upper arm fluidic belt (preferably filled with a circulating liquid coolant at a precisely controlled temperature gradient), two upper thigh fluidic cuff and belt assemblies, each upper thigh fluidic cuff and belt assembly comprising an upper arm blood pressure cuff and an upper arm fluidic belt, two arm sensor holders, each arm sensor holder supporting an arm sensor, and two leg sensor holders, each leg sensor holder supporting a leg sensor; a cooling and grounding unit, said cooling and grounding unit comprising a display having a user interface and a processor that is operated in accordance with a software program and said cooling and grounding unit being electrically connectable to a ground; and an umbilical cable that operably connects said components of said compression/cooling garment to said cooling and grounding unit. Preferably, said compression/cooling garment further comprises a suit comprising a first plurality of smart spheres, a left foot piece comprising a second plurality of smart spheres, a right foot piece comprising a third plurality of smart spheres and a head piece comprising a fourth plurality of smart spheres; each of said smart spheres comprises a heat exchanger that provides a circuitous path for coolant introduced to it; and each of said heat exchangers is a part of a separated cooling circuit that is connected to said cooling and grounding unit. Preferably, each arm sensor is capable of measuring a wrist pulse and each leg sensor is capable of measuring an ankle pulse. Preferably, each of said smart spheres further comprises a grounding contact, a pulse sensor and a temperature sensor; each grounding contact is connected to said cooling and grounding unit by a grounding lead and is operative to ground said human body; each said pulse sensor is operative to send a pulse signal to cooling and grounding unit; and each said temperature sensor is operative to send a temperature signal to cooling and grounding unit.

In a preferred embodiment, at least a portion of said first plurality of smart spheres is located in a part of said suit that is disposed adjacent to the spine of said human body when said apparatus is in use. Preferably, each of said blood pressure cuffs is in air pressure communication with said cooling and grounding unit and each of said fluidic belts is in fluidic communication with said cooling and grounding unit. Preferably, said cooling and grounding unit comprises a compressor and a condenser and said umbilical cord connects said compression garment to said compressor and to said condenser. Preferably, each arm sensor comprises a clip-on finger pulse sensor and each leg sensor comprises a clip-on toe pulse sensor.

In another preferred embodiment, the invention is an apparatus for treating an exercising human body, said exercising human body having a core body temperature and limbs having blood vessels, said apparatus comprising: means for lowering the core body temperature of the exercising human body; means for compressing the blood vessels of the exercising human body; and means for grounding the exercising human body.

In yet another preferred embodiment, the invention is a method for increasing the vascular performance during an exercise protocol of a human body having extremities, said method comprising: measuring an initial systolic blood pressure and an initial pulse in each extremity of the human body; measuring the core body temperature of the human body; lowering the core body temperature of the human body to about 96 degrees Fahrenheit; establishing a target blood pressure in each extremity of the human body by applying a pressure in the range from about 178 mm Hg to about 238 mm Hg to each extremity with a band that is disposed around each extremity, said target blood pressure being approximately 120 percent of the initial systolic blood pressure in each extremity; establishing a target pulse each extremity of the human body, said target pulse being detectable during the exercise protocol; and grounding the human body.

In a further preferred embodiment, the invention is a method for increasing vascular performance of a human body said human body having a core body temperature and upper arms and upper thighs having blood vessels, said method comprising: a step for lowering the core body temperature of the human body; a step for compressing the blood vessels of the upper arms and the upper thighs of the human body; and a step for grounding of the human body. Preferably, the method further comprises: using a coolant that is in a temperature range from about 44 degrees Fahrenheit to about 56 degrees Fahrenheit to lower the core body temperature by about 2 or 3 degrees Fahrenheit to about 96 Fahrenheit. Preferably, the method further comprises: compressing the blood vessels of the body's upper arms and upper thighs by applying a pressure in the range from about 178 mm Hg to about 238 mm Hg to the exterior of the upper arms and upper thighs of the body. Preferably, the method further comprises: lowering the core body temperature to about 96 degrees Fahrenheit. Preferably, the method further comprises: applying a maximum pressure of about 238 mm Hg to the upper arms and upper thighs for up to about six minutes.

In yet another preferred embodiment, the invention is a method for increasing the amount of growth hormone produced by a subject having limbs, said method comprising: the subject's donning a compression garment; connecting said compression garment to a core body cooling and grounding unit; measuring an initial blood pressure and an initial pulse rate in each of the limbs of the subject and confirming that the subject is grounded; commencing an exercise regime; circulating a coolant through said compression garment to produce a subsequent body temperature; and compressing a portion of each limb of the subject while monitoring a subsequent pulse and a subsequent blood pressure in each limb and said subsequent body temperature. Preferably, the method further comprises: controlling said subsequent blood pressure in each limb by applying a pressure in the range from about 178 mm Hg to about 238 mm Hg to the exterior of an upper portion of the limbs of the subject. Preferably, the method further comprises: lowering the body temperature of the subject by about 2 or 3 degrees Fahrenheit. Preferably, the method further comprising: lowering the body temperature of the subject to about 96 Fahrenheit.

In another preferred embodiment, the invention is a method of minimizing swelling after injury of a subject, said method comprising: placing the subject on a stretcher that incorporated smart spheres that are imbedded in memory foam; and lowering the temperature of the head, neck and spine of the subject by about 2 or 3 degrees Fahrenheit by circulating a coolant through said smart spheres; wherein each of said smart spheres comprises a heat exchanger that provides a circuitous path for coolant introduced to it; and wherein each of said heat exchangers is a part of a separate cooling circuit that is connected to a cooling and grounding unit.

In another preferred embodiment, the invention is an apparatus for enveloping and immobilizing an injured person, said apparatus comprising: an inflatable compression garment comprising two flaps that are attachable to one another by a zipper or belts and individual temperature control units; and a cooling unit comprising a compressor and a condenser; wherein each of said individual temperature control units comprises a heat exchanger that provides a circuitous path for coolant introduced to it; and wherein each of said heat exchangers is a part of a separated cooling circuit that is connected to said cooling and grounding unit.

In yet another preferred embodiment, the invention is an apparatus for increasing driving comfort of a user, said apparatus comprising: a vehicle seat for supporting the user that comprises an integral seat bottom heat exchanger and an integral seat back heat exchanger; a safety belt for securing the user in said seat that comprises an integral safety belt heat exchanger; a pair of inflatable upper arm belts for encircling the upper arms of the user; a pair of inflatable upper thigh belts for encircling the upper thighs of the user; means for measuring the initial systolic blood pressure of the user; and means for cyclically inflating said pair of inflatable upper arm belts and said pair of upper thigh belts to a inflation pressure that is approximately thirty percent greater than said initial systolic blood pressure at a cyclic inflation frequency that is in the range from about thirty times per minute to about sixty times per minute.

In a further preferred embodiment, the invention is a method for increasing driving comfort of a user, said method comprising: supporting the user in a vehicle seat that comprises an integral seat bottom heat exchanger and an integral seat back heat exchanger; securing the user in said seat with a safety belt that comprises an integral safety belt heat exchanger; encircling each of the upper alms of the user with an inflatable upper arm belt; encircling each of the upper thighs of the user with an inflatable upper thigh belt; measuring the initial systolic blood pressure of the user; and cyclically inflating said pair of inflatable upper arm belts and said pair of upper thigh belts to a inflation pressure that is approximately thirty percent greater than said initial systolic blood pressure at an inflation frequency that is in the range from about thirty times per minute to about sixty times per minute.

In another preferred embodiment, the invention is a method for increasing the performance of a swimmer, said method comprising: encircling each of the upper arms of the swimmer with an inflatable upper arm belt; encircling each of the upper thighs of the swimmer with an inflatable upper thigh belt; measuring the initial systolic blood pressure of the user; and cyclically inflating said pair of inflatable upper arm belts and said pair of upper thigh belts to a inflation pressure that is approximately thirty percent greater than said initial systolic blood pressure at an inflation frequency that is in the range from about thirty times per minute to about sixty times per minute.

Further aspects of the invention will become apparent from consideration of the drawings and the ensuing description of preferred embodiments of the invention. A person skilled in the art will realize that other embodiments of the invention are possible and that the details of the invention can be modified in a number of respects, all without departing from the concept. Thus, the following drawings and description are to be regarded as illustrative in nature and not restrictive.

BRIEF DESCRIPTION OF THE SEVERAL VIEWS OF THE DRAWINGS

The features of the invention will be better understood by reference to the accompanying drawings which illustrate presently preferred embodiments of the invention. In the drawings:

FIG. 14 is a side elevation view of another preferred embodiment of the invention.

Figure 1:
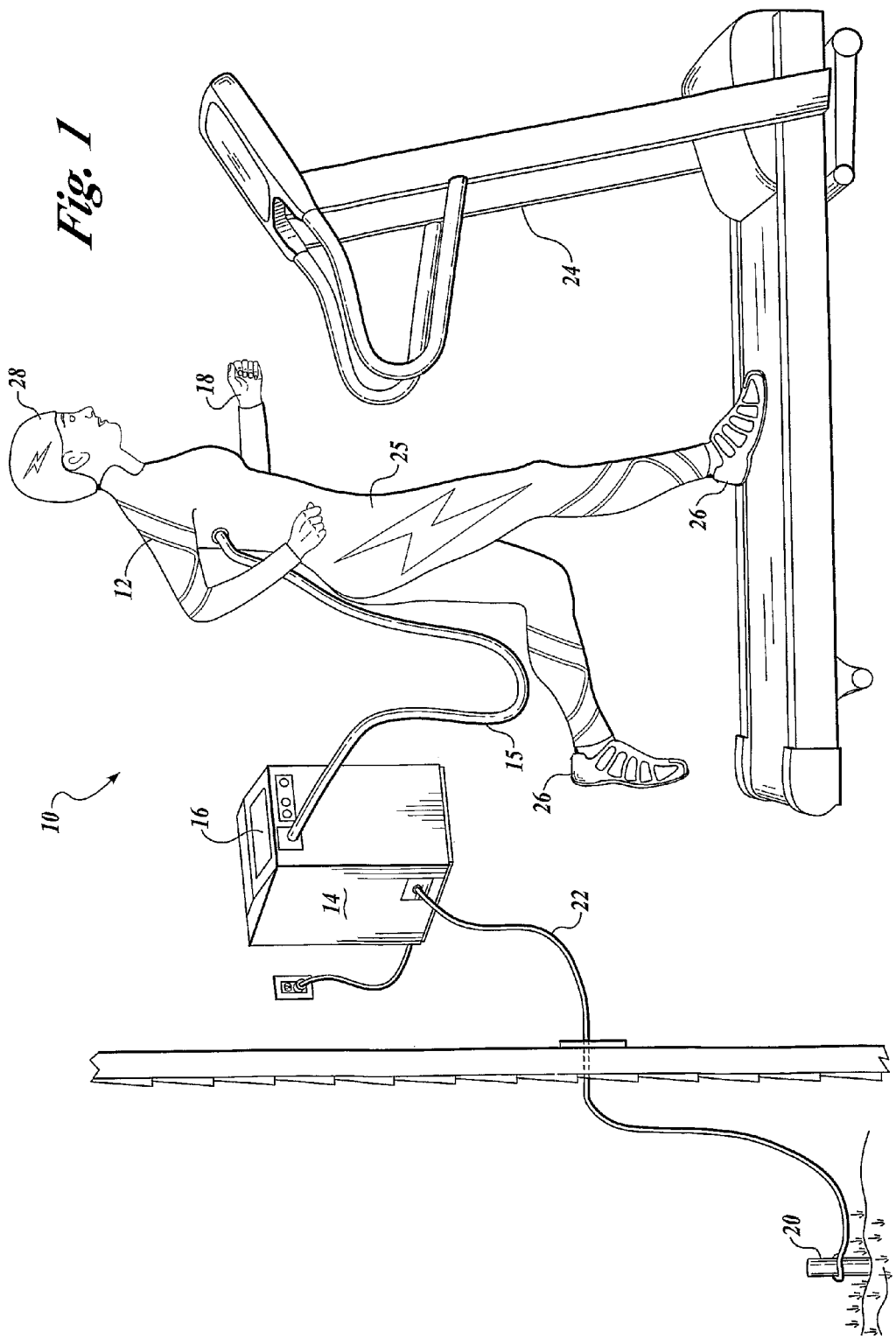
FIG. 1 is a perspective view of a preferred embodiment of the invention, shown in use.

The following reference numerals are used to indicate the parts and environment of the invention on the drawings:

10 apparatus
12 compression wear, compression garment, compression/cooling garment
14 cooling and grounding unit
15 umbilical cable
16 display
18 body
20 rod
22 conductor
24 exercise machine
25 suit
26 foot pieces
28 hat piece
30 smart spheres, individual cooling units
32 foot covering
34 sole
36 inlet tubes
38 outlet tubes
42 blood pressure cuffs
44 belts, inflatable belts, fluidic belts
46 sensor holders, bands
50 sensors
51 tubing bundles
52 longitudinal zippers
54 circuitous path
58 leads
60 cuff and belt assembly
62 fluidic tubing
64 air tubing
66 gurney, patient transport unit
80 vehicle seat
82 integral seat heat exchangers
84 safety belt heat exchanger
86 safety belt

DETAILED DESCRIPTION OF THE INVENTION

Referring to FIG. 1, a preferred embodiment of system 10 is illustrated. In this embodiment, apparatus 10 comprises: compression garment 12 and cooling and grounding unit 14 comprising display 16 having a user interface and a processor (not shown) that is operated in accordance with a software program that is resident in a memory unit (not shown). Compression garment 12 is connected to cooling and grounding unit 14 by umbilical cable 15. Treatment of body 18 of a human subject serves to maximize human performance and minimize rehabilitation time. In a preferred embodiment, cooling and grounding unit 14 is grounded by being connected to grounded rod 20 by conductor 22.

In use during exercise on exercise machine 24, apparatus 10 accomplishes cooling, vascular restriction (compression) and electron transfer (grounding) of body 18 with significant rehabilitative, fitness and restorative benefits. In a preferred embodiment, compression wear 12 comprises one suit 25, two foot pieces 26 and one hat piece 28.

Pain, muscle spasms, tissue damage and swelling are reduced by specific changes to the core body temperature by apparatus 10. Core cooling of body 18 with apparatus 10 also allows for significantly more efficient vascular restriction during exercise that is proven to increase the natural secretion of growth hormones by body 16.

Figure 2:
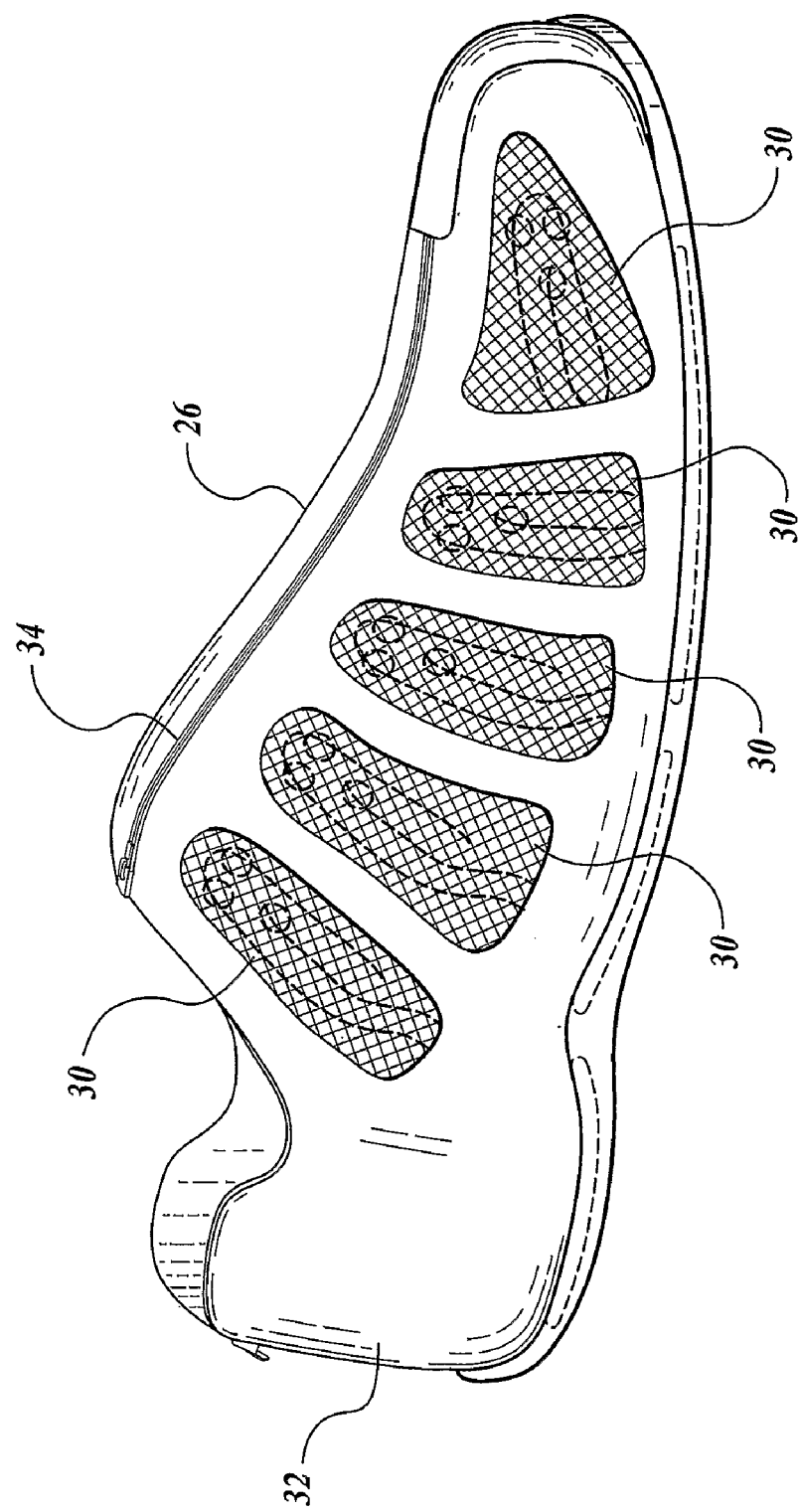
FIG. 2 is a perspective view of a foot piece of a preferred embodiment of the invention.

Referring to FIG. 2, one of the foot pieces 26 is illustrated. Foot covering 26 comprises a plurality of smart spheres that are mounted in foot covering 32. Zipper 34 provided a means to open foot covering 32.

Figure 3:
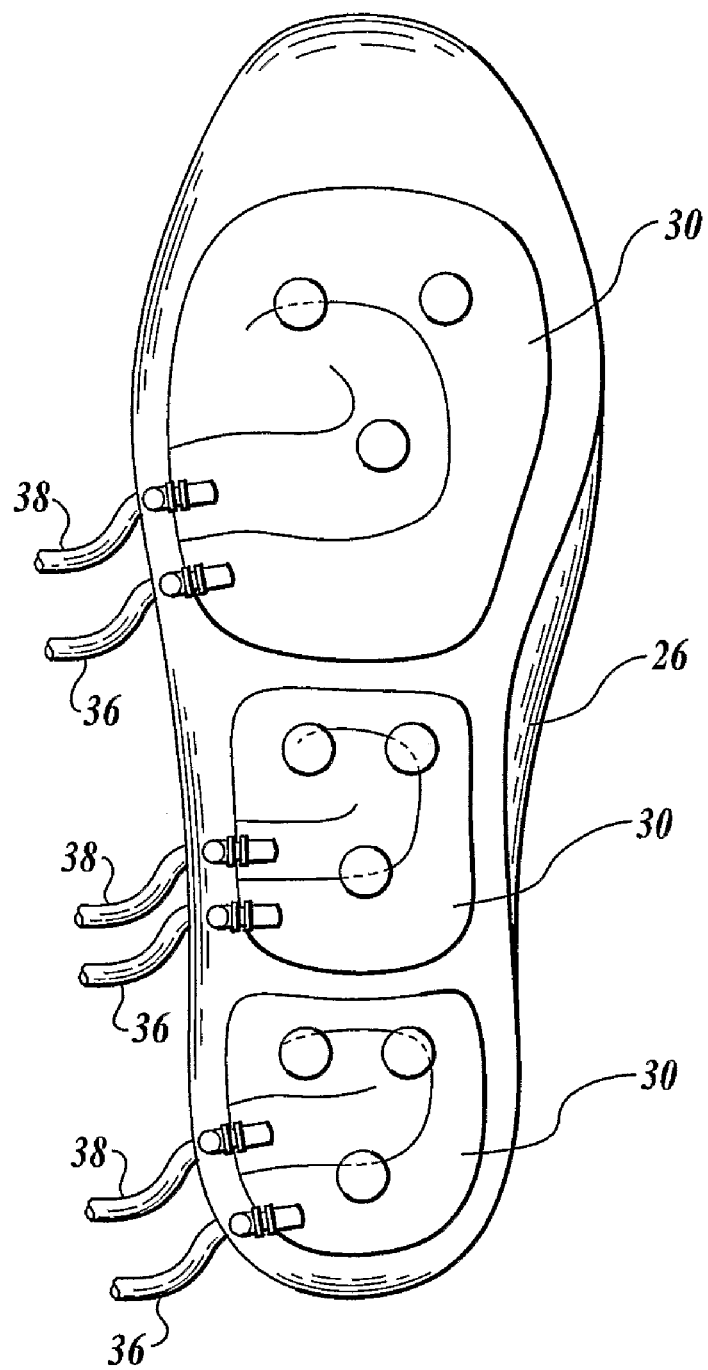
FIG. 3 is a bottom plan view of a foot piece of a preferred embodiment of the invention.

FIG. 3 presents a bottom view of one of the foot pieces 26 in accordance with a preferred embodiment of the invention. In this view, the smart spheres 30 are shown mounted in sole 34. Smart spheres are preferably not spherical in shape, but rather are substantially hollow bladders. As is the case with all preferred smart spheres 30, these smart spheres 30 have a lower surface (not shown) that is disposed adjacent to the surface of body 18 when in use. Preferably, each smart sphere is connected to cooling and grounding unit 14 by inlet tube 36 and outlet tube 38. Coolant (not shown) flowing in inlet tube 36 enters one of the smart spheres 30, circulates through a preferably circuitous path within the smart sphere 30 and then exits through outlet tube 38. In a preferred embodiment, the rate of flow of coolant circulating through each of the smart spheres 30 or each of the group of smart spheres 30 in suit 25, hat piece 28 and each of the foot pieces 26 is individually controlled by means of cooling and grounding unit 14.

Figure 4:
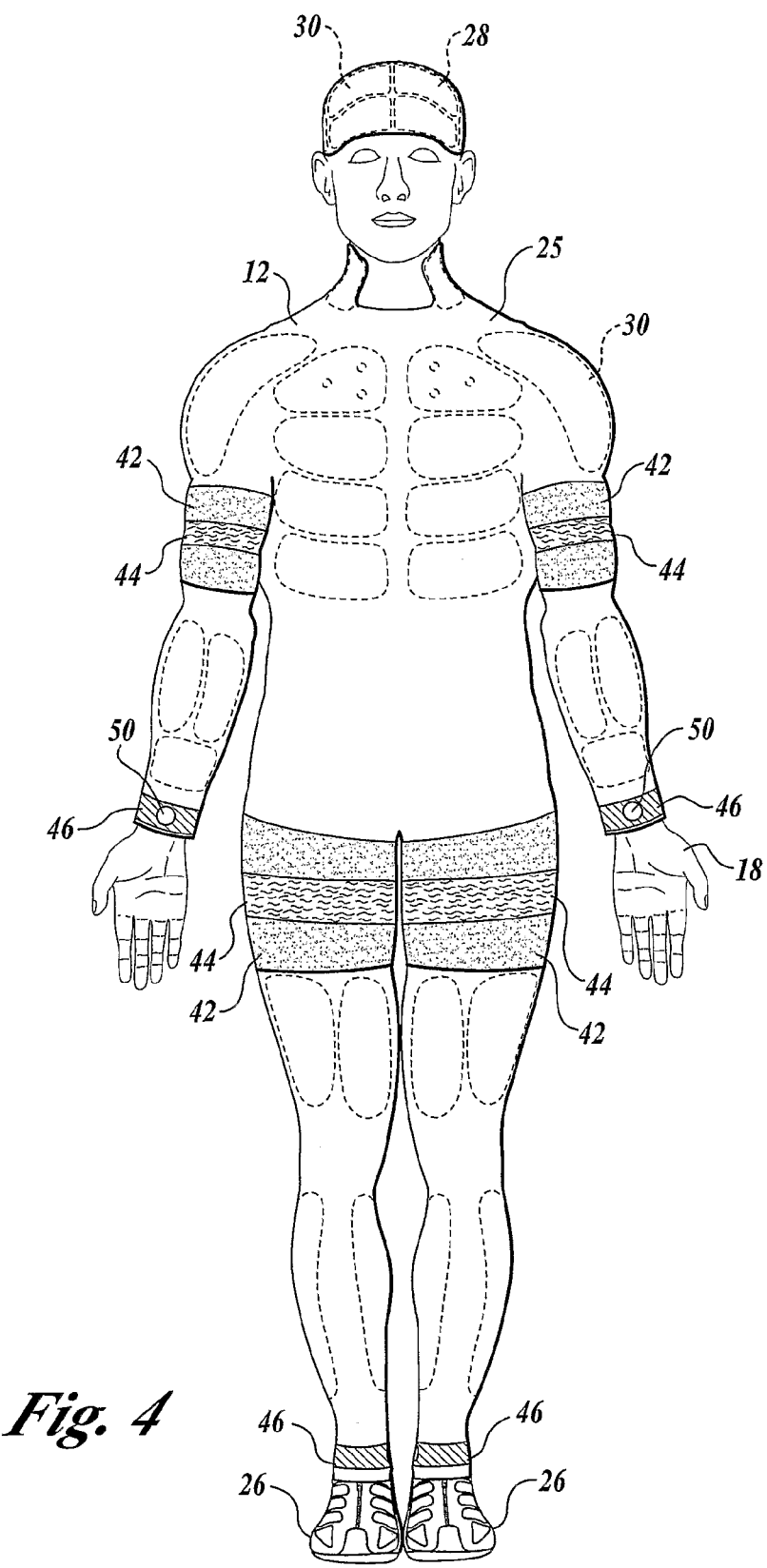
FIG. 4 is a front elevation view of the compression garment a preferred embodiment of the invention.

Referring to FIG. 4, a front view shows compression garment 12 installed on body 18. Suit 25 of compression garment preferably comprises a plurality of smart spheres 30 (indicated with dashed lines), four blood pressure cuffs 42 (indicated with solid lines), four belts 44 (indicated with a first pattern), four sensor holders or bands 46 (indicated with a second pattern) and four sensors 50 (two of which are shown as solid dots, the others being located in the ankle bands).

Figure 5:
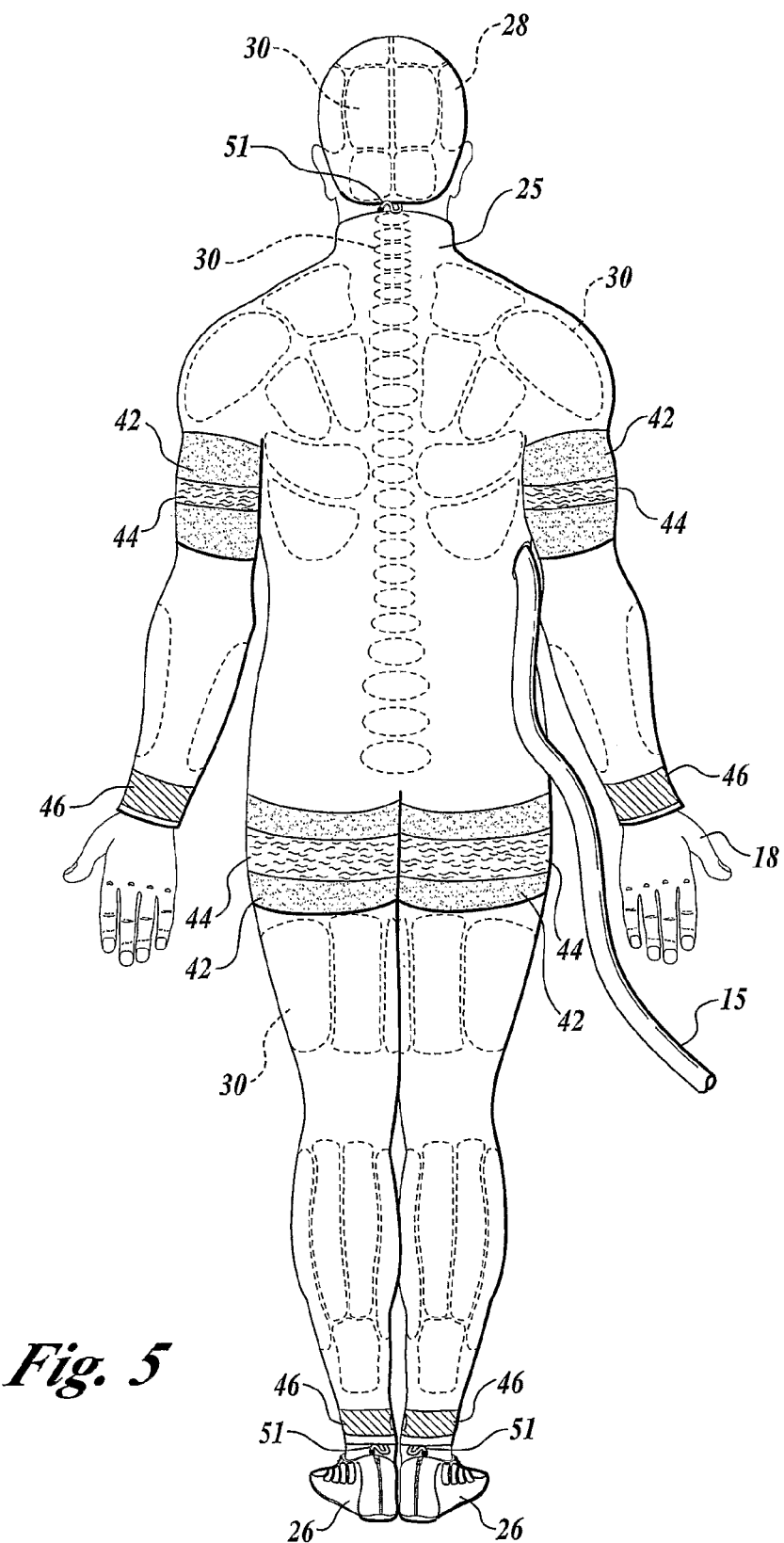
FIG. 5 is a back elevation view of the compression garment a preferred embodiment of the invention.

Referring to FIG. 5, a back view shows compression garment 12 installed on body 18. Suit 25 of compression garment preferably comprises a plurality of smart spheres 30 (shown in dashed lines) that are located along the spine of body 18. Tubing bundles 51 are shown to connect the components of compression garment 12. By locating a series of smart spheres 30 along the spine of body 18, an effective amount of cooling of the cerebral spinal fluid is achieved using coolant that is maintained at a lower temperature than would otherwise be used. In a preferred embodiment, the shapes of the smart spheres 30 at are disposed along the spine are configured to match the contour of body 18 and maximize heat transfer by conduction.

In the case of use of apparatus 10 to treat a spinal injury, cooling of the injured area can lower the metabolic rate (in that not as much blood is needed to supply spinal tissues). This technique can be used to reduce the ordinarily massive amount of lymphatic fluid that is directed by body 18 to the injured area. This in turn can reduce swelling and allow new connections among spinal tissues to be established after injury to the spine. Similarly, use of apparatus 10 can reduce the increase in pressure on the brain that often results from a skull injury, pressure that can reduce the amount of blood that reaches the brain, in some cases causing brain death. Thus, a reduction in swelling (due to mild hypothermia and other effects produced by use of apparatus 10) can save spinal cord and brain function.

In an alternative embodiment, compression garment 12 is configured to allow cooling of the head, neck and spine of body 18, lowering the metabolic rate of those body parts and minimizing swelling after injury. In another alternative embodiment, smart spheres 30 that are embedded in memory foam are incorporated into a stretcher and located adjacent to the spine and neck and surrounding the head of the injured person being transported in the stretcher.

In another alternative embodiment, an inflatable version of compression garment 12 is used to envelope and immobilize an injured person. In this embodiment, compression garment 12 comprises two washable flaps that are held together by a zipper or belts. The pressure on body 18 exerted by inflating compression garment 12 has the effect of minimizing bleeding. In such mobile embodiments, grounding of body 18 may not be provided for or accomplished.

In another alternative embodiment, apparatus 10 comprises a plurality of core body cooling spheres 30 that are built into an automobile seat. Conduction core cooling of body 18 occurs when it was seated in the seat, thus eliminating the need for air conditioning.

Figure 6:
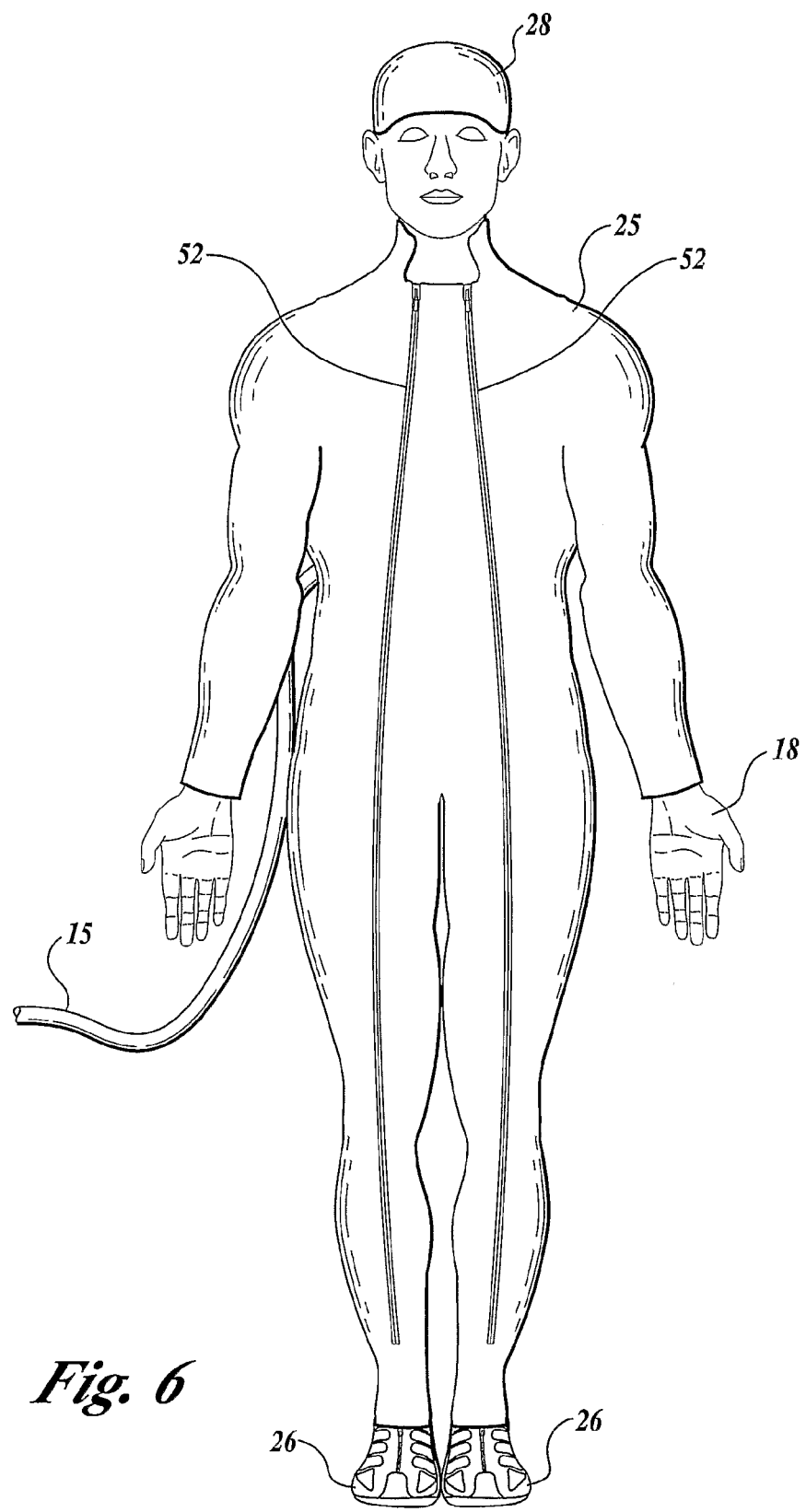
FIG. 6 is another front elevation view of the compression garment a preferred embodiment of the invention.

Referring to FIG. 6, a preferred embodiment of compression garment 12 is installed on body 18. In this embodiment, access to suit 25 is shown to be by means of two longitudinal zippers 52. In this embodiment, compression garment 18 covers essentially all of body 18 except the hands and face. In an alternative embodiment, compression garment 12 covers only the torso and head of body 18. The pair of belts 44 that encircle the upper legs of body 18 preferably have two ends that are joined either by means of longitudinal zippers 52 or more preferably by separate clasps (not shown) or Velcro® fasteners (not shown). The pair of blood pressure cuffs 42 that encircle the upper legs of body 18 also have two ends that are preferably joined by separate clasps (not shown) or Velcro® fasteners (not shown).

Figure 7:
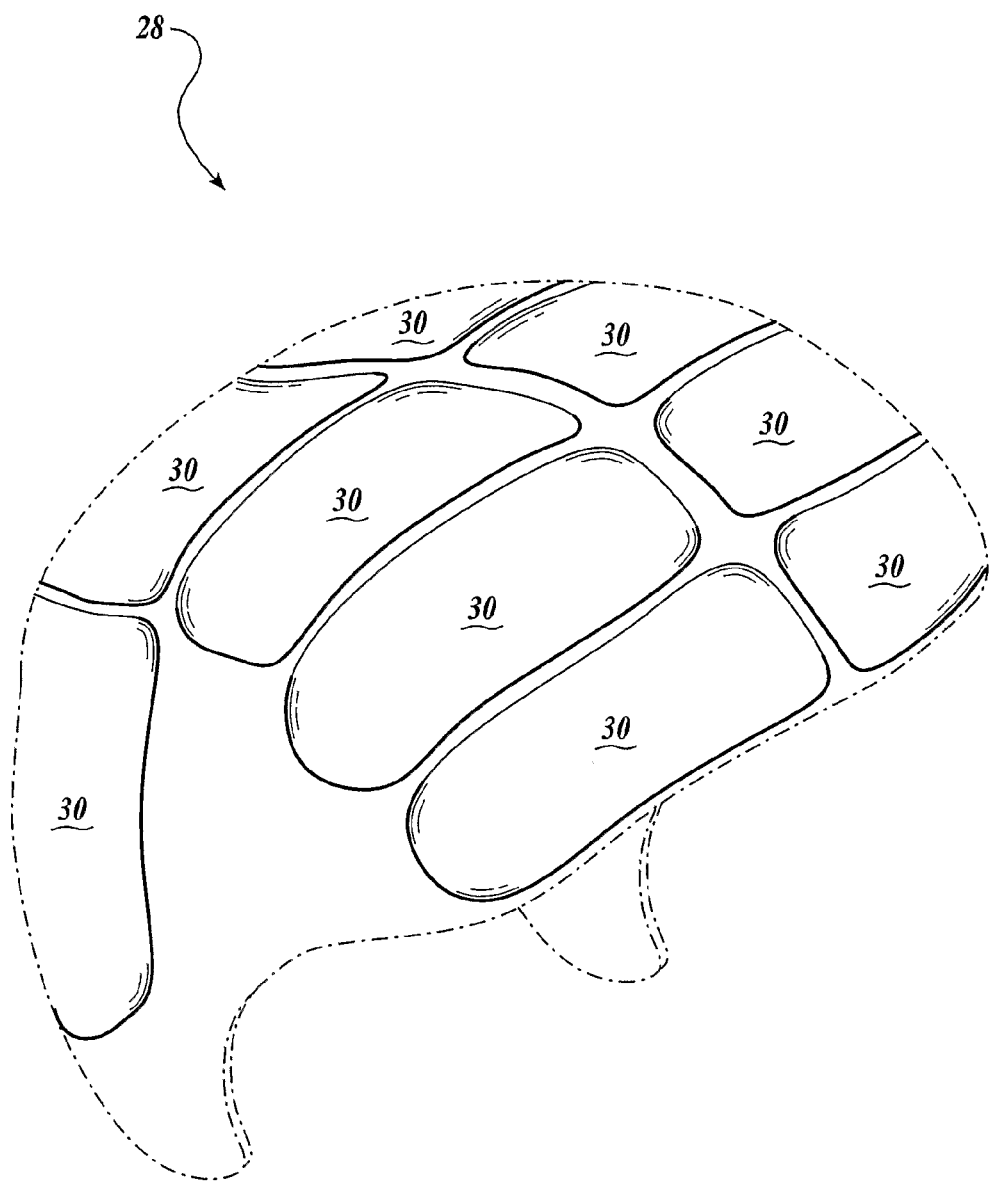
FIG. 7 is a perspective view of the head piece of a preferred embodiment of the invention.

Referring to FIG. 7, a perspective view of hat piece 28 is shown. A plurality of smart spheres 30 are mounted in hat piece 28. In a preferred embodiment, each of the smart spheres 30 is supplied with coolant by cooling and grounding unit 14 and the coolant is circulated through each of the smart spheres 30 or each group of smart spheres 30 in a separate cooling circuit that is connected by means of a valve to a manifold (not shown) that is mounted in cooling and grounding unit 14.

Figure 8:
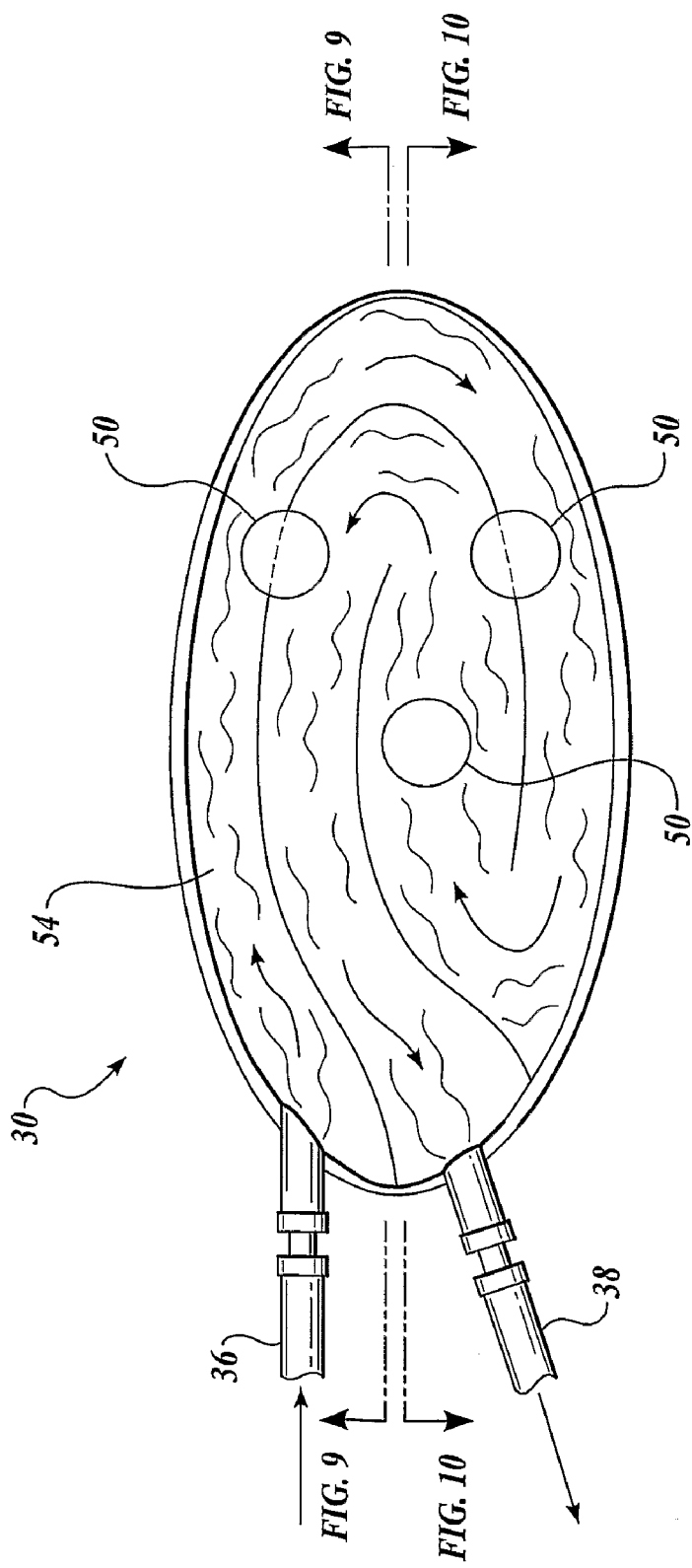
FIG. 8 is a top plan view of a smart sphere of a preferred embodiment of the invention.
Figure 9:
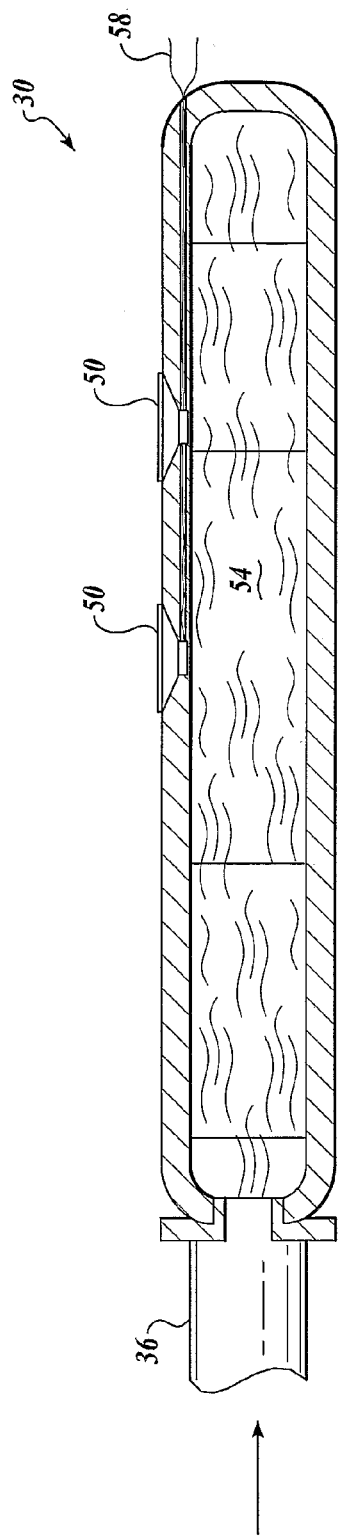
FIG. 9 is a cross sectional view of a smart sphere of a preferred embodiment of the invention, at the section indicated on FIG. 8.
Figure 10:
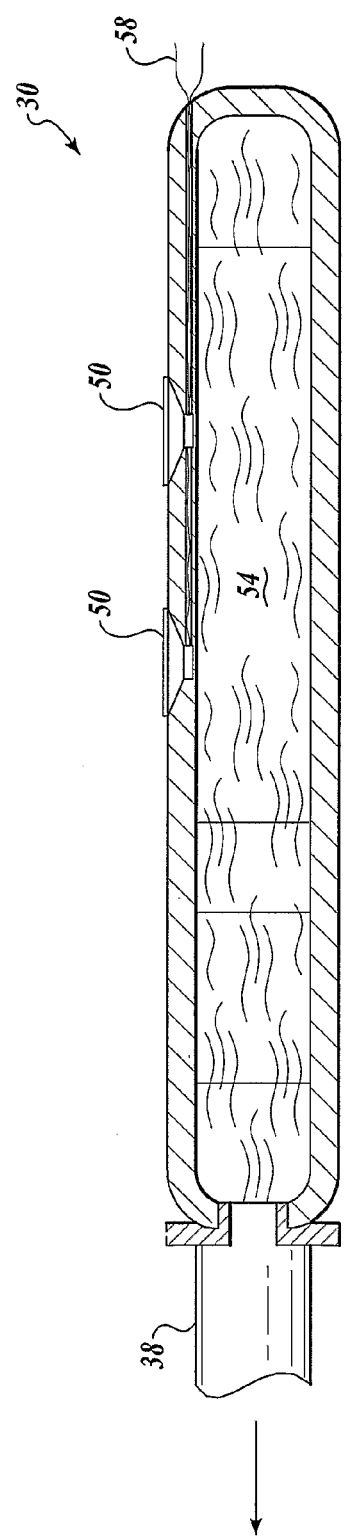
FIG. 10 is another cross sectional view of a smart sphere of a preferred embodiment of the invention, at the section indicated on FIG. 8.

Referring to FIGS. 8-10, a preferred embodiment of smart sphere 30 is presented. As is the case with all preferred smart spheres 30, these smart spheres 30 are connected to cooling and grounding unit 14 by inlet tube 36 and outlet tube 38. Coolant (not shown) flowing in inlet tube 36 enters one of the smart spheres 30, circulates through circuitous path (e.g., a labyrinth) within the smart sphere 30 and then exits through outlet tube 38. In a preferred embodiment, the rate of flow of coolant circulating through each of the smart spheres is individually controlled by means of cooling and grounding unit 14. A plurality of sensors 50 are shown mounted on the exterior surface of smart sphere 30 that is in contact with body 18 when apparatus 10 is in use. Sensors 50 are in communication with cooling and grounding unit 14 by means of leads 58. In a preferred embodiment, all of sensors 50 are in contact with the skin of body 18 and one of sensors 50 is a grounding contact, a second of sensors 50 is a pulse sensor and a third of sensors 50 is a temperature sensor. In a preferred embodiment, each temperature sensor is a conventional thermocouple. Sensors 50 are located within compression garment 12 so as to allow a pulse to be taken at each extremity of body 18, e.g., at each wrist and at each ankle. In a preferred embodiment, each smart sphere 30 is embedded in memory foam, indicated with cross hatching on FIGS. 9 and 10. In a preferred embodiment, the coolant comprises medical grade propylene glycol, a surfactant (e.g., Jet Dry® manufactured by Reckitt Benckiser Inc. of Parsippany, N.J.), iodine and distilled water.

Figure 11:
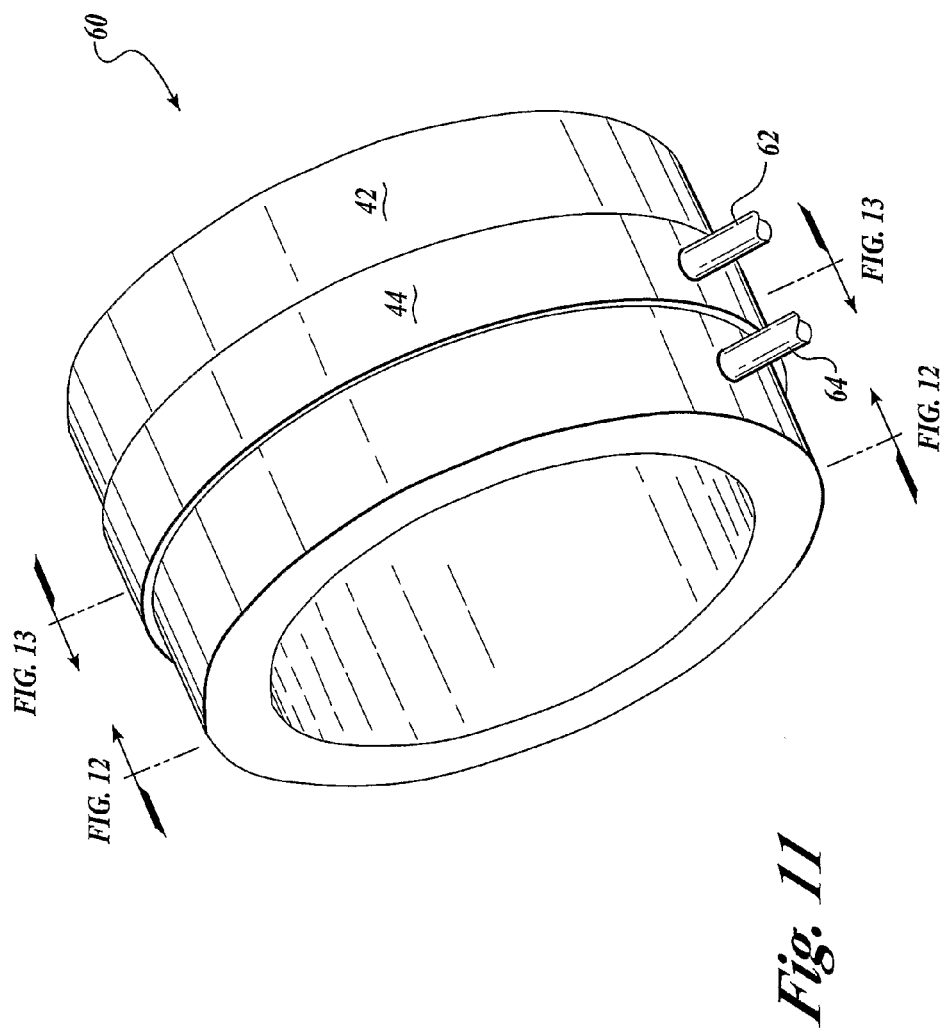
FIG. 11 is a perspective view of a cuff and belt assembly of a preferred embodiment of the invention.
Figure 12:
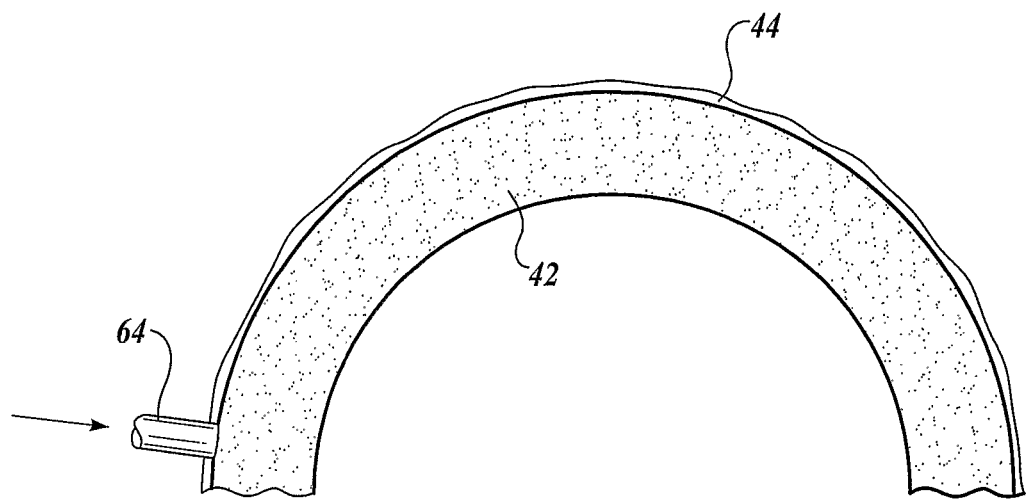
FIG. 12 is a cross sectional view of a cuff and belt assembly of a preferred embodiment of the invention, at the section indicated on FIG. 11.
Figure 13:
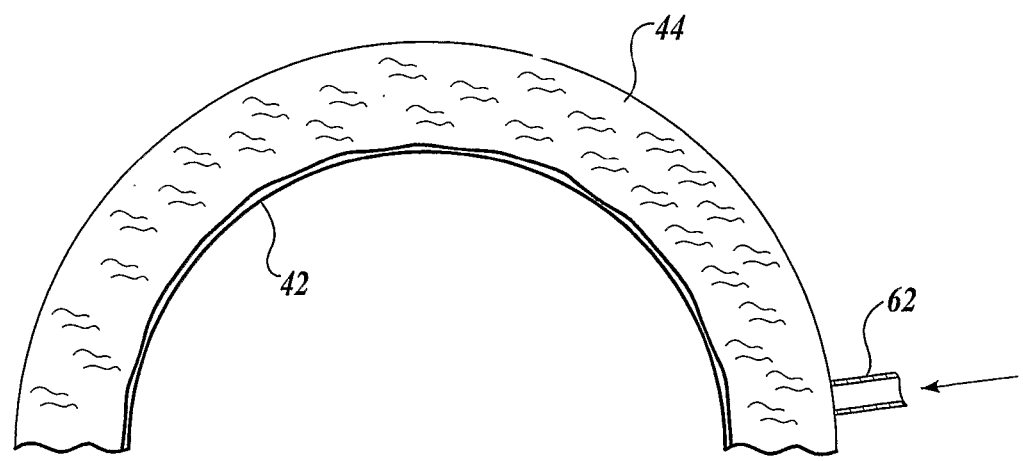
FIG. 13 is another cross sectional view of a cuff and belt assembly of a preferred embodiment of the invention, at the section indicated on FIG. 11.

Referring to FIG. 11, a perspective view of cuff and belt assembly 60 is presented. Cross sectional views of cuff and belt assembly 60 are presented in FIGS. 12 and 13 which reveal the layered nature of cuff and belt assembly 60. In this embodiment, cuff and belt assembly 60 comprises blood pressure cuff 42 and belt 44. In a preferred embodiment, the version of belt 44 that is used on the legs of body 18 is about two inches wide and about 28 inches long. Preferably, the version of belt 44 that is used on the arms is about one inch wide and about 16 inches long. In FIG. 11, blood pressure cuff 42 is shown inflated and in FIG. 12 belt 44 is shown deflated. Each blood pressure cuff 42 is preferably in air pressure communication with core body cooling and grounding unit 14 via air tubing 64. In a preferred embodiment, each blood pressure cuff 42 is a conventional blood pressure cuff and is in communication with a sphygmomanometer (not shown) in cooling and grounding unit 14. Each inflatable belt 44 is preferably in fluidic communication with cooling and grounding unit 14 via fluid tubing 62. In an alternative embodiment, the pulse in each extremity is measured by means of a conventional clip-type (clip-on) pulse sensor that is applied to a finger or toe of body 18.

Operation of apparatus 10 involves checking the blood pressure, pulse and temperature of each extremity of body 18 before and after each exercise activity involving compression, cooling and grounding. At the beginning of each activity, each blood pressure cuff 42 is inflated (pressurized with air or liquid coolant) sequentially (one after the other) until the blood flow (and hence, pulse) in that extremity is reduced. Then, the pressure within the blood pressure cuff 42 is decreased until a pulse is detected by the appropriate pulse sensor 50, indicating that the pressure in the cuff 42 is equal to the systolic pressure in that extremity. At that point, the cuff 42 is deflated. After the blood pressure and pulse rate are measured in each extremity, each of the inflatable bands 44 is inflated (pressured with a liquid), preferably until a target blood pressure in the extremity is reached. The liquid pressure within each band 44 is preferably controlled by means of a fluidic valve (not shown) that is mounted in cooling and grounding unit 14. In a preferred embodiment, during the exercise activity, the fluid pressure in each band 44 is controlled to limit the blood pressure in each extremity to no more than about 120 percent of the initially measured blood pressure. Moreover, during the exercise activity, the pulse in each extremity is monitored and the fluidic pressure in the band 44 that is reducing blood circulation in that extremity is decreased or released (decreased to zero) if the monitored pulse in the extremity becomes reduced in rate or weak.

Apparatus 10 allows the reduction of the core temperature of body 18 during exercise with reduced blood circulation in the extremities of body 18. This reduction in core body temperature reduces the pain that is usually associated with reduced blood circulation in extremities of body 18 to manageable levels. Core body cooling also increases the blood density, which allows less pressure to be applied to body 18 to reduce blood circulation. Although the applicant does not wish to be held to any particular theory of operation of apparatus 10, he believes that after a month of exercise activity using apparatus 10, increased levels of human growth hormone are present in body 18. Body 18 responds to the heightened levels of human growth hormone by growing another blood flow system (more blood vessels) in its extremities.

In another alternative embodiment, compression wear 12 comprises fluidic belts 44 that cause vascular constriction at the upper arms and upper legs. In this embodiment, belts 44 have a hooks and loops closure, e.g., a Velcro® closure. During exercise, this quickly leads to lactic acid accumulation and forces the blood into normally unused capillaries. After body 18 senses that its muscles contain lactic acid, extra growth hormones are produced and carried by the blood throughout the entire body.

In a preferred embodiment, apparatus 10 is grounded to the earth during use. Grounding of body 18 by apparatus 10 creates a conductive path between the user of apparatus 10 and the earth. Grounding allows the earth's free electrons to flow to the body in order to maintain its natural free electron balance. This helps restore the body's natural electrical state so that chronic pain can immediately subside. In a preferred embodiment, body 18 is grounded by means of a separate grounding circuit which is provided between each smart sphere 30 and the ground via umbilical cable 15. Preferably, the grounding circuit for body 18 does not go through a conventional electrical receptacle.

In use, apparatus 10 allows the human subject using it to achieve lower core body temperature and increase the blood density. These effects are accomplished via a compliant heat exchanger in the form of a matrix of individual temperature control units, termed smart spheres. Each smart sphere adheres to the skin surface and removes the heat through heat exchange with the surface blood vessels. The same blood vessels are used as a vehicle to deliver the cooling temperature to the core of body 18, thus lowering the core body temperature. As the temperature of body 18 decreases, the blood density is increased in a proportional manner.

In a preferred embodiment, apparatus 10 absorbs heat from the outer surface of human body 18 by utilizing a conventional refrigerant cycle, with a resulting reduction in body temperature. In this embodiment, body heat input to the liquid in smart spheres 30 is transferred to a refrigerant, which absorbs the heat by boiling, to produce a vapor. This vapor is directed to a compressor that compresses the vapor and then to a condenser which simultaneously absorbs heat from the compressed vapor and rejects heat to the atmosphere. This causes the refrigerant to liquefy, and expand through an expansion valve, prior to being reintroduced to smart spheres 30. By maintaining a given condenser pressure, the compressor loses its capacity as the intake pressure decreases, until a balance point is reached in which heat absorbed by smart sphere 30 (acting as a heat exchanger) matches the heat input to the heat exchanger.

In a preferred embodiment, the refrigerant (coolant) is supplied to body thermal panels 12 at a temperature in the range from 44 degrees Fahrenheit (F) to 54 degrees F., in order to lower the core body temperature of the user to the range to about 96 degrees Fahrenheit (F). This temperature setting may be overridden, if desired.

In a preferred embodiment, apparatus 10 applies pressure in the range from about 178 mm Hg to about 238 mm Hg to the blood vessels of the upper arms and upper thighs of the user in order to decrease the blood flow during the performance of an exercise protocol. Application of pressure on these blood vessels during exercise utilizing apparatus 10 causes body 18 to produce increased amounts of growth hormone in order to grow additional blood vessels and to provide adequate delivery of blood flow to the region within which blood flow is restricted. When a consistent regiment of exercise with vascular pressure is practiced, in time, additional "collateral circulation" is formed with the addition to the existing blood vessels, thus increasing overall blood flow in the region within which blood flow has been restricted. Increase in growth hormone secretions by body 18 results in a number of beneficial effects due to the presence of elevated growth hormone levels, such as increased metabolic rate, reduction of fat, increase in muscle size and strength, and overall increases in levels of human performance.

In a preferred embodiment, apparatus 10 achieves ground contact of body 16 during the performance of an exercise protocol. During exercise, significant amounts of static electricity are generated by body 16. Because body 16 operates on a bio/electrical principle, externally added high levels of static electricity interfere with and weaken the normal bio-electrical body functions, unless this extra electrical charge is released to the ground. Electrical ground contact also allows the transmission of neutral electrons from the earth to body 16, thus balancing the body's natural bio/electrical levels. In a preferred embodiment, smart spheres 30 sense whether grounding has been achieved and grounding status of body 18 is displayed on display 16 prior to the start of the treatment protocol.

Referring again to FIGS. 4 and 5, compression garment 12 is shown to comprise a plurality of individual smart spheres 30. Preferably, individual smart spheres 30 can be combined in any shape in a piece of clothing or equipment used to practice the methods disclosed herein. Preferably, each smart sphere 30 has its own flow and temperature control and it is imbedded in a memory foam. Thus, compression garment 12 is quite comfortable to wear.

In a preferred embodiment, the software program that operates apparatus 10 comprises instruction that cause apparatus 10 to perform a number of process steps. In one step, the subject puts on compression garment 12. In another step, garment 12 is connected to cooling and grounding unit 14. In another step, display 16 on cooling and grounding unit 14 shows the blood pressure and pulse rate of the subject and confirms that a connection to ground has been established. In another step, the subject sits on a stationary bicycle or stands on a treadmill and selects an exercise protocol. In another step, apparatus 10 starts the cooling cycle and applies compression while monitoring the pulses, temperatures and pressures of the subject. In another step, the subject continues the exercise protocol until the timer on cooling and grounding unit 14 tells him to stop. In another step, at the completion of the exercise protocol, the subject removes compression garment 12 and either stores the sensed data (e.g., pulses, temperatures, pressures) in the cooling and grounding unit or downloads it to a remote computer. All of the functions of apparatus 12 are displayed in a digital formal and can also be enunciated in a voice format.

Referring to FIG. 14, another preferred embodiment of apparatus 10 is shown in use in an emergency medical (ambulance) application for treatment of spine and head injuries. In this embodiment, apparatus 10 further comprises gurney or patient transport unit 66. Cooling and grounding unit 14 does not provide grounding of body 18 when apparatus 10 is being moved, but may provide grounding when apparatus 10 is stationary. In this embodiment, smart spheres 30 are preferably provided in head piece 28 and along the spine of body 18 and may be provided in other locations in garment 12.

Figure 16:
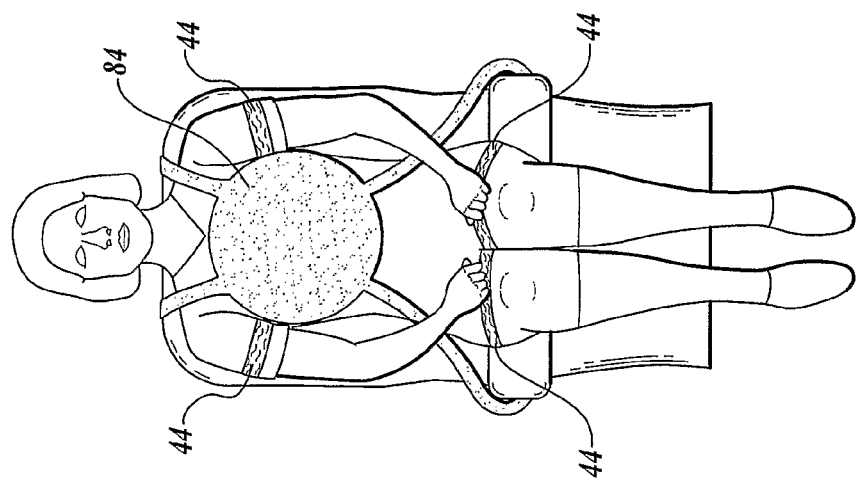
FIG. 16 is a front elevation view of the preferred embodiment of the invention illustrated in FIG. 15.
Figure 15:
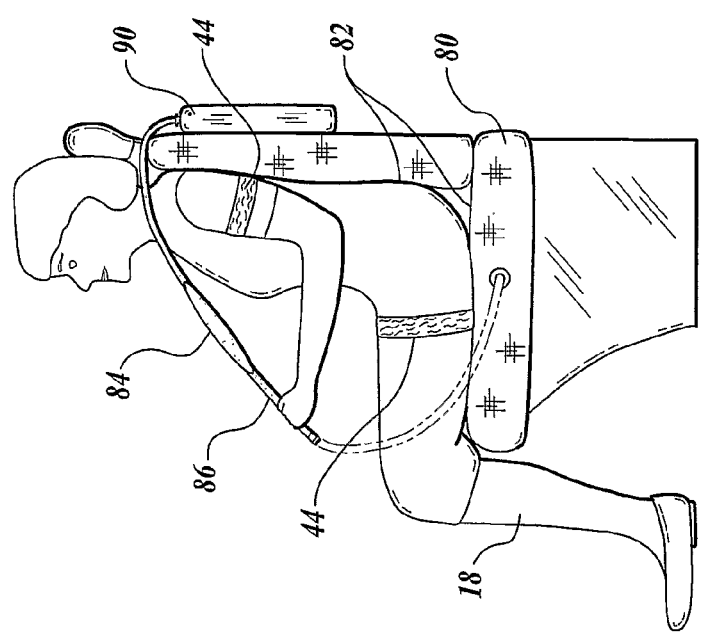
FIG. 15 is a side elevation view of yet another preferred embodiment of the invention.

Referring to FIGS. 15 and 16, another preferred embodiment of the invention is illustrated. In this embodiment, the user's body 18 is seated on vehicle seat 80 which is preferably temperature controlled by means of integral seat (e.g., back and bottom) heat exchangers 82 and safety belt heat exchanger 84 which is integral to safety belt 86. Circulation of a fluid through heat exchangers 82 and 84 ensures that the core body temperature of the user is closely regulated.

In this embodiment, inflatable belts 44 preferably encircle the upper arms and upper thighs of the user. These belts are preferably inflated to a pressure that is approximately thirty percent greater than the systolic blood pressure of the user in a cyclic manner. Preferably, pressure is applied to body 18 at a frequency that is in the range from about thirty times per minute to about sixty times per minute, with a more preferred frequency being about thirty times per minute. This cyclic vascular compression process of the limbs simulates walking. Operation of the system is controlled by human interface 90.

Cyclic vascular compression can also be used to simulate walking while the user is swimming. In this embodiment, the inflatable belts 44 that encircle the upper arms and upper thighs of the user are inflated cyclically as described above. This cyclic vascular compression increases venous blood flow and thereby increases oxygenation of the muscles in the swimmer's arms and legs.

Many variations of the invention will occur to those skilled in the art. Some variations include cooling, compression and grounding of one body part. Other variations call for cooling, compression and grounding of more than one body part. All such variations are intended to be within the scope and spirit of the invention. In the case of portable variations of this invention, grounding may not be possible while apparatus 10 is being moved.

Although some embodiments are shown to include certain features, the applicant(s) specifically contemplate that any feature disclosed herein may be used together or in combination with any other feature on any embodiment of the invention. It is also contemplated that any feature may be specifically excluded from any embodiment of the invention.

What is claimed is:

1. An apparatus having:
    a plurality of cuffs for application to a human body, each cuff having:
        a support belt having an adjustable diameter;
        a pressure inlet and a pressure outlet coupled to a flexible bladder, said bladder formed to have an increased fluidic path length from said inlet to said outlet, said bladder having a first surface for coupling pressure to and in thermal exchange with a human body encircled by said support belt, a second surface opposite said first surface and restrained by said support belt;
    a chiller having an outlet for pressurized fluid and a fluid return, said chiller outlet coupled to each said cuff pressure inlet, said chiller fluid return coupled to each said cuff pressure outlet;
    where said chiller provides a fluid pressure sufficient to reduce blood circulation and a fluid temperature sufficient to reduce blood temperature in a human body in need thereof;
    and where a maximum said pressure is established by measuring a subject human subject systolic blood pressure, and establishing said maximum pressure at less than or equal to 122 percent of said systolic blood pressure.

2. The apparatus of claim 1 where said fluid pressure and said fluid temperature are applied for a sufficient duration of time to result in the increased generation of human growth hormone in a patient in need thereof and having at least one limb enclosed by at least one of said cuffs.

3. The apparatus of claim 1 where at least two of said cuffs have said adjustable diameter which includes a diameter of one or more human extremities.

4. The apparatus of claim 1 where at least two of said cuffs have said adjustable diameter which includes the diameter of a human arm.

5. The apparatus of claim 1 where at least two of said cuffs have said adjustable diameter which includes the diameter of a human leg.

6. The apparatus of claim 1 having four cuffs, two said cuffs having said adjustable diameter which includes the diameter of a human upper arm and two said cuffs having said adjustable diameter which includes the diameter of a human thigh.

7. The apparatus of claim 1 where said fluid contains at least one of water or air.

8. The apparatus of claim 1 where said pressure is in the range 178 mm Hg to 238 mm Hg.

9. The apparatus of claim 1 where said temperature is sufficient reduce a core body temperature of a human subject.

10. The apparatus of claim 1 where said pressure varies over time.

11. The apparatus of claim 1 where said chiller includes an earth electrical connection which is coupled to at least one said cuff first surface.

12. The apparatus of claim 1 where said chiller is also coupled to a vest for application to a human torso, said vest removing heat from a human subject.

13. A process for using an adjustable cuff having a flexible bladder, an inlet port coupled to said flexible bladder, an outlet port coupled to said flexible bladder, said flexible bladder having a subject contact surface and an opposing restraint surface coupled to an adjustable belt, the process having the steps:
    applying said adjustable cuff to the thighs and optionally upper arms of a human subject;
    applying a pressure to said inlet port and said outlet port of at least one of said cuffs sufficient to reduce blood circulation in the legs or arms associated with a respective said cuff;
    where said inlet port pressure is greater than said outlet port pressure, thereby forming a fluid flow;
    and where said fluid flow and said pressure are selected to increase the human growth hormone production in a human subject in need thereof.

14. The process of claim 13 where said cuff inlet port and said cuff outlet port are coupled to a chiller for generating said inlet pressure and said fluid flow, thereby removing heat from said patient.

15. The process of claim 13 where said adjustable cuffs are provided to said upper arms and said lower legs, and said inlet port pressure is in the range 178 mm Hg to 238 mm Hg.

16. The process of claim 13 where said applying pressure to said inlet step includes making a systolic blood pressure measurement, thereby establishing a maximum pressure of 122 percent of said systolic blood pressure.

17. An apparatus for the enhanced production of human growth hormone in a human subject, the apparatus having:
- a plurality of pressurized cuffs for encircling the limbs of a human subject and reducing the blood circulation therein, the cuffs having:
  - a support belt having an adjustable diameter;
  - a pressure inlet and a pressure outlet coupled to a flexible bladder, said bladder formed to have an increased fluidic path length from said inlet to said outlet, said bladder having a first surface for coupling pressure to and in thermal exchange with an encircled limb, a second surface opposite said first surface and restrained by said support belt;
- a chiller having an outlet for pressurized fluid and a fluid return, said chiller outlet coupled to each said cuff pressure inlet, said chiller fluid return coupled to each said cuff pressure outlet;
- a grounding electrode for electrically connecting a human to earth;
- a thermal bladder for coupling to a human subject, said thermal bladder coupled to said chiller and removing heat from a human subject;
- where said chiller provides a fluid pressure to said cuffs sufficient to reduce blood circulation and a fluid temperature sufficient to reduce blood temperature, and said chiller provides a fluid temperature and flow to said thermal bladder sufficient to reduce the core temperature of a human subject;
- and where a maximum cuff pressure is established by measuring a subject human subject systolic blood pressure, and establishing said maximum cuff pressure at less than or equal to 122 percent of said systolic blood pressure.

18. The apparatus of claim 17 where each said pressurized cuff operates with a pressure less than 122 percent of the systolic blood pressure of an encircled limb.

19. The apparatus of claim 17 where said chiller pressure and fluid temperature are selected for improved human growth hormone production.

20. An apparatus having:
- a plurality of cuffs for application to a human body, each cuff having:
  - a support belt having an adjustable diameter;
  - a pressure port coupled to a pressure bladder encircled by said support belt, said pressure bladder having a first surface for coupling bladder pressure to a human subject and a second surface opposite said first surface restrained by said support belt;
  - a fluid inlet and a fluid outlet coupled to a flexible bladder, said bladder formed to have an increased fluidic path length from said inlet to said outlet, said bladder having a first surface in thermal exchange with a human subject encircled by said support belt,
- a chiller having an outlet for pressurized fluid and a fluid return, said chiller outlet coupled to at least one said cuff fluid inlet, said chiller fluid return coupled to a corresponding said cuff fluid outlet thereby generating a fluid flow;
- a pressure source coupled to at least one said pressure port;
- where said pressurized fluid or gas has a pressure sufficient to reduce blood circulation in a human subject, and said chiller provides a fluid temperature sufficient to reduce blood temperature in a human subject;
- and where said cuff first surface includes an earth electrical connection.

21. The apparatus of claim 20 where said pressure source is air.

22. The apparatus of claim 20 where said pressure port pressure and said fluid inlet temperature and flow are selected to increase human growth hormone in a human subject.

23. The apparatus of claim 20 where a maximum said pressure is established by measuring a human subject systolic blood pressure, and establishing said maximum pressure at less than or equal to 122 percent of said systolic blood pressure.

* * * * *